United States Patent [19]

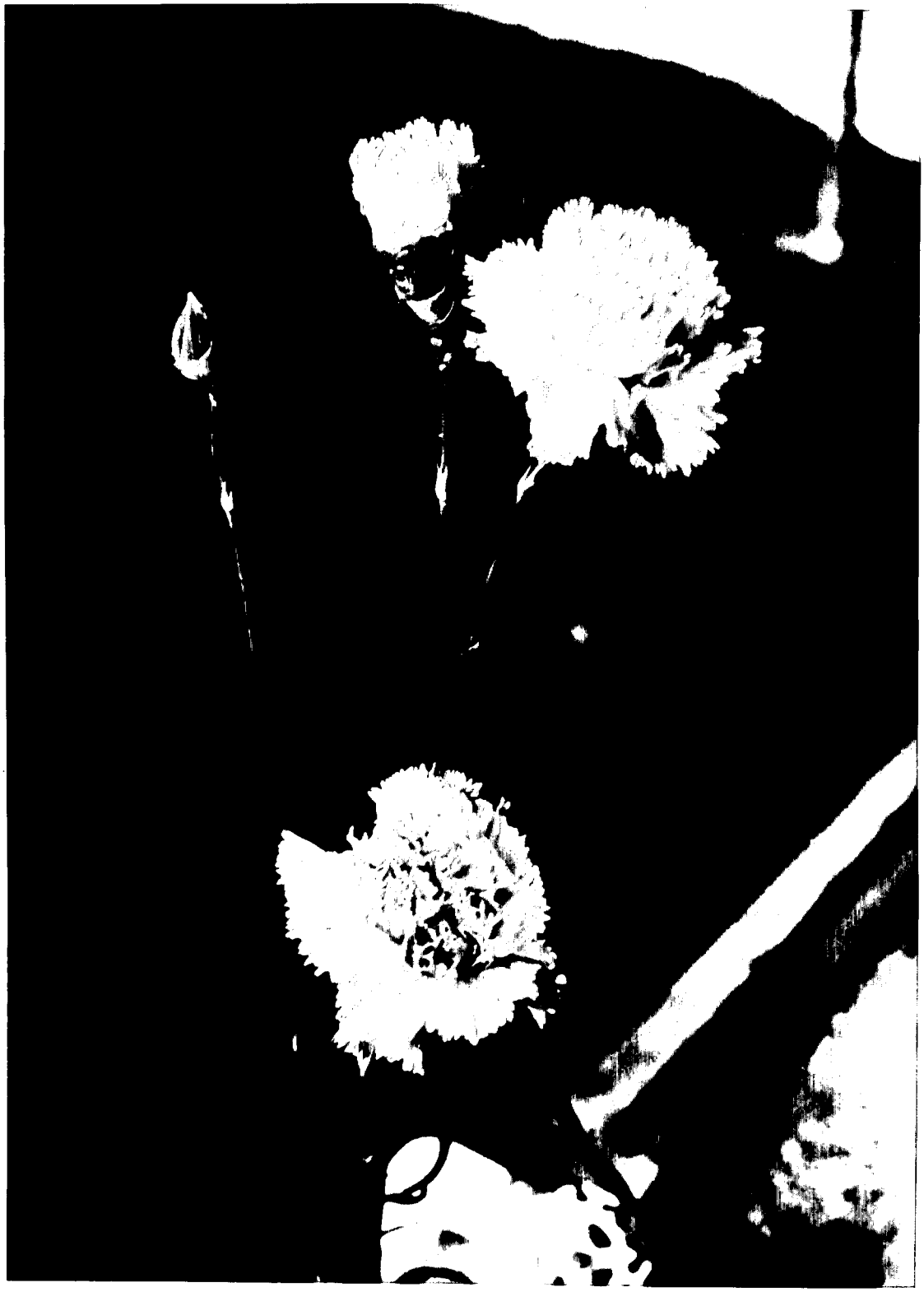

Carrier

[11] Patent Number: Plant 5,753

[45] Date of Patent: Jun. 24, 1986

[54] CARNATION PLANT 'GOLD METAL'

[76] Inventor: Leonard E. Carrier, 1911 Sheridan Rd., Encinitas, Calif. 92024

[21] Appl. No.: 654,727

[22] Filed: Sep. 27, 1984

[51] Int. Cl.[4] ..... A01H 5/00
[52] U.S. Cl. ..... Plt./70
[58] Field of Search ..... Plt./70

*Primary Examiner*—James R. Feyrer
*Attorney, Agent, or Firm*—James R. Cypher

[57] ABSTRACT

The present invention relates to a new and distinct cultivar of carnation plant, named Gold Metal, originated by me by irradiating Carrier's Fiesta, U.S. Plant Pat. No. 5,410, distinguished from its parent as well as any other variety known to me by its Gold-Buff-Yellow color, its superior resistance to soil borne diseases, and its flowers that open fully without bursting the calyx and causing splits.

1 Drawing Figure

BACKGROUND OF THE INVENTION

The present invention relates to a new and distinct cultivar of carnation plant, named Gold Metal which was originated by me by irradiating Carnation Plant, named Carrier's Fiesta, U.S. Plant patent application, Ser. No. 06/525,601, filed June 22, 1983 now U.S. Plant Pat. No. 5,410.

Typically, carnation plants, botanically known as the species *Dianthus caryophyllus,* are very prone to fungi and root rots, and have a tendency to burst their calyx causing "splits" as the flowers open fully. The new cultivar was the result of an irradiation program to develop carnations of "new" color with greatly improved resistance to soil-borne diseases and bursting of the Calyx. I selected for irradiation a cultivar developed by me earlier, named Carrier's Fiesta, U.S. Plant Pat. No. 5,410, which had shown improved resistance to soil-borne diseases and splitting, and irradiated it to obtain the new cultivar, Gold Metal. The parentage of the selected Carrier's Fiesta was by cross breeding numbered but unnamed and unpatented seedlings, nursery numbers 1981 and 1743.

These objectives were fully achieved in the new cultivar. It is very much like its predecessor Carrier's Fiesta, except in color, and of all the carnation plants known to me, it is most alike in characteristics to its predecessor Carrier's Fiesta.

The principal characteristics which are outstanding in my new cultivar, and which distinguish it from its predecessor, Carrier's Fiesta, as well as from all other carnations of which I am aware are as follows:

1. Superior resistance to soil-borne diseases such as *Fusarium oxysporium,* and *F. roseum* and root-rots such as damping off, water molds, and the like;
2. Large serrated flowers which open fully without bursting the calyx and causing "splits";
3. A distinctive and attractive Gold Yellow flower color with a few marginal flecks of Nepal Red.

Asexual reproduction of my new carnation variety by side shoot cuttings rooted in peat and "Perlite" under mist, as performed under my direction and control at Encinitas, Calif., shows that the foregoing characteristics and distinctions come true and are established and transmitted through succeeding propagations.

BRIEF DESCRIPTION OF THE DRAWING

The accompanying color photograph shows typical specimens of the new cultivar in different stages of development (tight buds, partially opened bud and full bloom) and illustrates the vigorous, free-breaking growth habit and strong, straight stems.

The color photo submitted is the one that Applicant feels most nearly shows the true color of his new cultivar, and close inspection of the two larger blooms shows the dark pink stripe in the petals of the flowers.

DETAILED DESCRIPTION OF THE DRAWING

The following is a detailed description of my new carnation cultivar, Gold Metal with color terminology in accordance with Robert Ridgway's Color Standards and Nomenclature (1912 edition).

The following detailed botanical description is based on observations of plants grown inside my commercial greenhouses at Encinitas, Calif.: the height of plant and flower and foliage size established as an average using standard commercial cultural practices.

The data provided accurately characterizes the cultivar in question. Color designation and other values stated may deviate slightly from the stated values from flowering to flowering, but the deviations will be within the range expected from varying environmental, seasonal, and cultural conditions.

Plant:

*Botanical classification.—Dianthus caryophyllus.*

*Breeding.*—Irradiation of Carnation Plant, Carrier's Fiesta, U.S. Plant Pat. Ser. No. 06/525,601, filed June 22, 1983.

*Form.*—Erect but free-branching.

*Growth.*—Vigorous and very free-branching.

*Height.*—Medium tall, approximately 80 to 100 cm.

*Classification.*—Greenhouse type, suitable for cut flower production as a standard (one bloom per stem).

*Propagation.*—Holds its distinguishing characteristics through succeeding propagations by rooted cuttings.

*Locality where grown and observed.*—Encinitas, Calif.

*Disease resistance.*—The new cultivar has shown no evidence of fusariums or other root rots, as determined by extensive tests in high infested soils inoculated with as many strains of fungi as are locally available in the area of Encinitas, Calif.; tests conducted without chemical or steam sterilization of the soil (soils in which the carnation plant "Sim" and others soon die).

*Blooming period.*—The new cultivar will bloom at any time of the year in California.

*Temperature tolerance.*—Not hardy to cold and will freeze at −10° C. Grows best at 10° C. but has good resistance to hot weather in summer months without hardening of growth and with only little reduction in flower size and fading.

Bud: Lobes of calyx overlap in tight bud and seldom split.

*Length.*—2.5 cm.

*Diameter.*—2.5 cm.

Bloom:

*Size.*—8 cm. diameter, depth 2.5 cm.

*Stem.*—Consists of 9 nodes. Length is about 60 cm. Diameter is about 0.8 cm. at base and about 0.4 cm. at base of calyx.

Color is Yew green Plate XXXI 27″ G-Y m. Yew green.

*Form.*—Generally round with high, well developed crown when fully opened, calyx is completely hidden.

*Petalage.*—From 80–90 petals. Outer petals are approximately 4.0 cm. wide and about 5.0 cm. long. Center petals are about 2.0 cm. wide and about 4.0 cm. long.

*Color.*—The center of flower, outer petals, base of petals, Plate 3, Pale ORG-Yellow 17-OY, back of petals Plate 15, 15′ Y-O Ochracous Buff. A few petals have a dark pink streak, Plate I 3 O-R Nepal Red.

*General tonality.*—Gold-Buff-Yellow with a dark pink streak.

*Petals.*—Texture is soft but firm. Form: Outer petals nearly semi-circular with roughly uniform serrations of 0.4 cm. to 0.1 cm. deep, 6 to 8 per cm. Opening: Outer petals expand before the center petals. The calyx is very strong and there is a minimum of split calyx.

*Fragrance.*—No distinctive fragrance.

Foliage :

*Form.*—Concave to flat.

*Size.*—1 cm. wide and 19 cm. long.

*Quantity.*—Two leaves per node, with nodes spaced about 5 cm. apart.

*Color.*—The upper and under sides of mature leaves are Yew green Plate XXXI 27″. G-Y M. Yew Green. New Growth Rainette Green 27″ G-Y i, Rainette Green.

*Texture.*—Smooth.

I claim:

1. A new and distinct cultivar of carnation plant named, Gold Metal substantially as herein shown and described, characterized particularly as to novelty by the unique combination of superior resistance to soil-borne diseases; large, slightly serrated flowers which open fully without bursting the calyx and causing "splits"; a distinctive and attractive Gold Buff-Yellow flower color which fades evenly and beautifully; a very vigorous and free-breaking plant habit; strong and straight stems; and good heat tolerance which is superior to that of the parent lines and the commercial standard, the so-called "Sim".

* * * * *